United States Patent

Broadhurst et al.

[11] Patent Number: 4,591,636
[45] Date of Patent: May 27, 1986

[54] ANTHRACYCLINE GLYCOSIDES

[75] Inventors: Michael J. Broadhurst, Baldock; Cedric H. Hassall, Harpenden; Gareth J. Thomas, Luton, all of Great Britain

[73] Assignee: Hoffmann-La Roche Inc., Nutley, N.J.

[21] Appl. No.: 682,448

[22] Filed: Dec. 17, 1984

Related U.S. Application Data

[63] Continuation of Ser. No. 280,718, Jul. 6, 1981, abandoned.

[30] Foreign Application Priority Data

Jul. 18, 1980 [GB] United Kingdom ............... 8023498
May 26, 1981 [GB] United Kingdom ............... 8116053

[51] Int. Cl.⁴ .......................................... C07H 15/252
[52] U.S. Cl. ................................. 536/6.4; 260/365; 556/7
[58] Field of Search ........................... 536/6.4

[56] References Cited

U.S. PATENT DOCUMENTS

| | | | |
|---|---|---|---|
| 3,970,641 | 7/1976 | Jolles et al. | 536/6.4 |
| 4,039,663 | 8/1977 | Arcamone et al. | 536/6.4 |
| 4,067,969 | 1/1978 | Penco et al. | 536/6.4 |
| 4,131,649 | 12/1978 | Penco et al. | 536/6.4 |
| 4,263,428 | 4/1981 | Apple et al. | 536/6.4 |
| 4,325,947 | 4/1982 | Penco et al. | 536/6.4 |

Primary Examiner—Johnnie R. Brown
Attorney, Agent, or Firm—Jon S. Saxe; Bernard S. Leon; Richard J. Mazza

[57] ABSTRACT

The invention relates to compounds of the formula

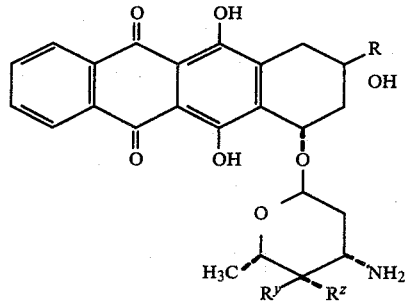

wherein R is lower alkyl or a carboxy group or a group of the formula

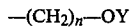 a —(CH$_2$)$_n$—OY in which n stands for 1 or 2 and Y is hydrogen or alkyl and R$^Y$ and R$^z$ each are hydrogen or one of R$^Y$ and R$^z$ is hydrogen and the other is hydroxy, and pharmaceutically acceptable acid addition salts thereof.

These compounds and salts possess antibiotic and antitumor activity and can be used as medicaments in the form of pharmaceutical preparations.

9 Claims, No Drawings

ANTHRACYCLINE GLYCOSIDES

This is a continuation of application Ser. No. 280,718 filed July 6, 1981, now abandoned, NOVEL GLYCOSIDES, Broadhurst et al.

DESCRIPTION OF THE INVENTION

The present invention relates to novel glycosides. More particularly, the invention is concerned with novel anthracycline glycosides, a process for the manufacture thereof and pharmaceutical preparations containing same.

The novel anthracycline glycosides provided by the present invention are compounds of the formula

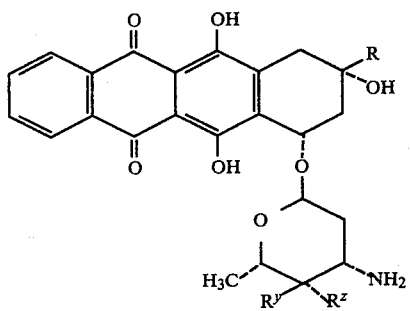

wherein R is lower alkyl or a carboxy group or a group of the formula $$-(CH_2)_n-OY \qquad a$$

in which n stands for 1 or 2 and Y is hydrogen or alkyl and $R^Y$ and $R^z$ each are hydrogen or one of $R^Y$ and $R^z$ is hydrogen and the other is hydroxy, and pharmaceutically acceptable acid addition salts thereof.

A preferred group of compounds of formula I comprises those in which R is lower alkyl or a group of formula (a) in which Y is hydrogen. Also preferred are compounds of formula I in which one of $R^Y$ and $R^z$ is hydrogen and the other is hydroxy.

Examples of preferred compounds of formula I hereinbefore are:

(1S)-cis-1-[(3-Amino-2,3,6-trideoxy-α-L-lyxohexopyranosyl)oxy]-1,2,3,4,6,11-hexahydro-3,5,12-trihydroxy-3-hydroxymethyl-6,11-dioxonaphthacene and (1S)-cis-1-[(3-amino-2,3,6-trideoxy-α-L-lyxohexopyranosyl)oxy]-1,2,3,4,6,11-hexahydro-3,5,12-trihydroxy-3-methyl-6,11-dioxonaphthacene.

(1S)-cis-1-[(3-amino-2,3,6-trideoxy-α-L-arabinohexopyranosyl)oxy]-1,2,3,4,6,11-hexahydro-3,5,12-trihydroxy-3-methyl-6,11-dioxonaphthacene, (1S)-cis-1-[(3-amino-2,3,6-trideoxy-α-L-arabinohexopyranosyl)oxy]-1,2,3,4,6,11-hexahydro-3,5,12-trihydroxy-3-hydroxymethyl-6,11-dioxonaphthacene and (1S)-cis-1-[(3-amino-2,3,6-trideoxy-α-L-lyxohexopyranosyl)oxy]-3-ethyl-1,2,3,4,6,11-hexahydro-3,5,12-trihydroxy-6,11-dioxonaphthacene.

According to the process provided by the present invention, the compounds of formula I hereinbefore and their pharmaceutically acceptable acid addition salts are manufactured by reacting a compound of the general formula

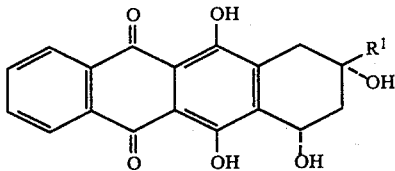

wherein $R^1$ is lower alkyl or an esterfied carboxy group or a group of the formula $$-(CH_2)_n-OY' \qquad a'$$

wherein n has the significance given earlier and Y' is lower alkyl or acyl with a compound of the formula

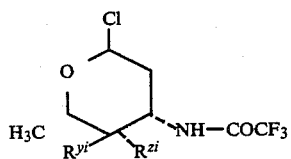

wherein $R^{Yi}$ and $R^{zi}$ each are hydrogen or one of $R^{Yi}$ and $R^{zi}$ is hydrogen and the other is a p-nitrobenzoyloxy group, cleaving off the protecting group or groups from the reaction product and, if desired, converting the resulting compound of formula I into a pharmaceutically acceptable acid addition salt.

As used in this Specification, the term "lower alkyl" means a straight-chain or branched-chain alkyl group which preferably contains from 1 to 6 carbon atoms such as methyl, ethyl, propyl, isopropyl, butyl, tert.butyl, pentyl, hexyl etc. An esterified carboxy group can be an alkoxycarbonyl group (e.g. methoxycarbonyl, ethoxycarbonyl etc), an aryloxycarbonyl group (e.g. phenoxycarbonyl etc) or an aralkoxycarbonyl group (e.g. benzyloxycarbonyl etc). The methoxycarbonyl group is the preferred alkoxycarbonyl group. An acyl group or the acyl moiety of an acyloxy group can be derived from an alkanecarboxylic acid (e.g. acetic acid, propionic acid etc), an aromatic carboxylic acid (e.g. benzoic acid etc) or an araliphatic carboxylic acid (e.g. phenylacetic acid etc). An aryl group can be, for example, phenyl, substituted-phenyl (e.g. methoxyphenyl), pyridyl etc.

The reaction of a compound of formula II with a compound of formula III in accordance with the process provided by the present invention can be carried out in a manner known per se. In a preferred embodiment, the reaction is carried out in an inert organic solvent and in the presence of a soluble silver salt. Examples of inert organic solvents which can be used are dichloromethane, dimethylformamide, tetrahydrofuran etc, with tetrahydrofuran being preferred. Preferably, the reaction is carried out at a low temperature (e.g. about −5° C.).

The protecting group or groups is/are then cleaved off from the reaction product of the formula

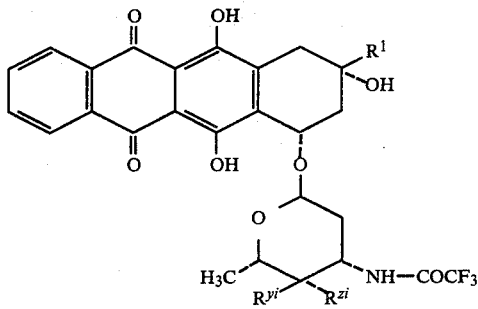

wherein $R^1, R^{Yi}$ and $R^{zi}$ are as above.

The cleavage of the protecting group or groups from a compound of formula IV can be carried out in a manner known per se; for example, by treatment with an aqueous alkali such as aqueous sodium hydroxide. It will be appreciated that when two protecting groups are present in a compound of formula IV, then the cleavage of such groups can be carried out in one or two steps by appropriate choice of cleavage conditions. Thus, in the two-step procedure the p-nitrobenzoyl protecting group can be cleaved off first followed by the trifluoroacetyl protecting group.

The compounds of formula I can be converted into pharmaceutically acceptable acid addition salts by treatment with pharmaceutically acceptable inorganic acids (e.g. hydrochloric acid, hydrobromic acid, sulphuric acid, phosphoric acid etc) and with pharmaceutically acceptable organic acids (e.g. acetic acid, tartaric acid, citric acid, fumaric acid, maleic acid, malic acid, methanesulphonic acid, toluene-4-sulphonic acid etc).

The compounds of formula I contain two asymmetric carbon atoms in the aglycone portion and it will be appreciated that the invention includes within its scope both the (1S)-cis compounds and (1R)-cis compounds.

The compounds of formula II hereinbefore used as starting materials in the process provided by the present invention can be prepared by subjecting a compound of the formula

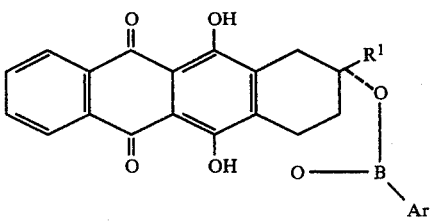

wherein $R^1$ is as above and Ar is aryl
to an ester-exchange with a 1,3-diol.

The aforementioned ester-exchange can suitably be carried out by reacting a compound of formula V with an excess of a 1,3-diol in the presence of an acid. An especially preferred 1,3-diol is 2-methyl-2,4-pentanediol. Preferred among the acids which can be used are the lower alkanecarboxylic acids such as acetic acid etc. The reaction is conveniently carried out in the presence of an inert organic solvent (e.g. a halogenated hydrocarbon such as dichloromethane etc) and at about room temperature.

The compounds of formula V hereinbefore can be prepared by de-acylating a compound of the formula

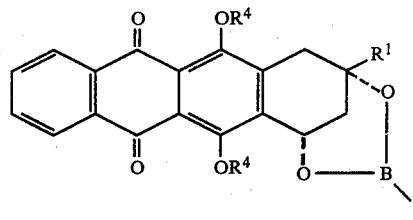

wherein $R^1$ and Ar are as above and $R^4$ is acyl.

The de-acylation of a compound of formula VI is preferably carried out using boron trichloride in an inert organic solvent (e.g. a halogenated hydrocarbon such as dichloromethane etc) and at a low temperature (e.g. at about $-10°$ C.). The de-acylation may be carried out by aqueous acid or base treatment under conventional conditions.

The compounds of formula VI hereinbefore can be prepared by oxidizing a compound of the formula

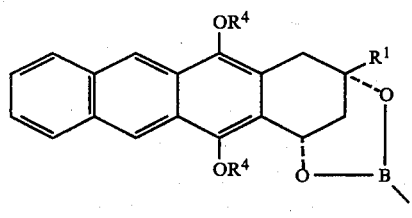

wherein $R^1, R^4$ and Ar are as above
with a chromic oxidizing agent under anhydrous conditions.

A preferred chromic oxidising agent for use in the foregoing oxidation is chromium trioxide. In a preferred embodiment, this oxidation is carried out in the presence of a mixture of an appropriate anhydrous carboxylic acid and the anhydride corresponding thereto (e.g. a mixture of glacial acetic acid and acetic anhydride). This oxidation can be carried out at a temperature between about room temperature and about 60° C., preferably at about room temperature.

The compounds of formula VII hereinbefore can be prepared by catalytically hydrogenating a compound of the formula

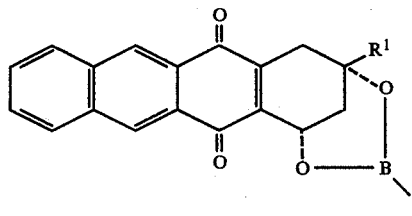

wherein $R^1$ and Ar are as above
under acylating conditions.

Suitable catalysts which may be used in the catalytic hydrogenation of a compound of formula VIII are noble metal catalysts such as, for example, palladium, platinum, ruthenium, rhodium etc. The catalyst may be supported on a suitable carrier material (e.g. palladium-on-carbon etc). The acylating conditions are provided by carrying out the catalytic hydrogenation in the presence of a suitable acylating agent, preferably a carboxylic acid anhydride such as acetic anhydride etc. A tertiary organic base is conveniently present in the mixture as an acid-binding agent. Included among the tertiary organic bases which can be used are tri(lower alkyl)amines such as triethylamine, pyridine, collidine etc. Pyridine is the preferred tertiary organic base. The catalytic hydrogenation is advantageously carried out at room temperature and at atmospheric pressure.

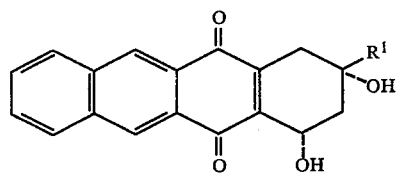

IX wherein $R^1$ is as above,
with an aromatic boronic acid.

The reaction of a compound of formula IX with an aromatic boronic acid is preferably carried out in an inert organic solvent. The preferred solvents are aromatic hydrocarbons such as benzene, toluene and xylene. Of the aromatic boronic acids which can be used in this reaction benzeneboronic acid is preferred. However, other aromatic boronic acids such as tolueneboronic acid, xyleneboronic acid, methoxybenzeneboronic acid, nitrobenzeneboronic acid, pyridineboronic acid or the like can also be used. It is convenient to carry out this reaction in the presence of a catalytic amount of a carboxylic acid, preferably a lower alkanecarboxylic acid such as acetic acid, propionic acid etc. The reaction is advantageously carried out at an elevated temperature, suitably at the reflux temperature of the reaction mixture.

It will be appreciated that, depending on the conditions used in carrying out the steps described hereinbefore for the preparation of compounds of formula II, an acyloxy group may be hydrolysed to a hydroxy group. When this occurs, the acyloxy group can be regenerated in accordance with methods known per se after the particular step has been carried out or at an appropriate later stage.

The compounds of formula IX hereinbefore can be prepared, for example, as shown in Formula Scheme I hereinafter in which $R^1$ has the significance given earlier and $R^5$ represents an acyloxy group.

Formula Scheme I

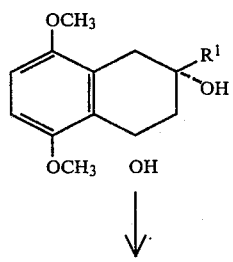

X

-continued
Formula Scheme I

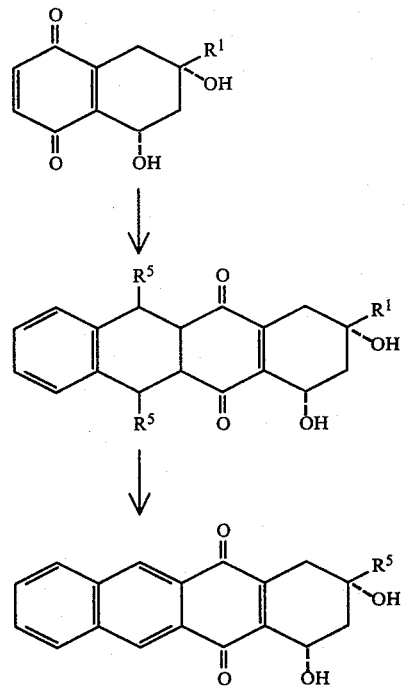

Having regard to the Formula Scheme I, a compound of formula X is converted into a compound of formula XI by treatment with ammonium ceric nitrate. This treatment is advantageously carried out in a mixture of water and a water-miscible organic solvent (e.g. acetonitrile or the like.) The treatment is advantageously carried out at about room temperature.

A compound of formula XI is then converted into a compound of formula XII by reaction with a trans compound of the formula

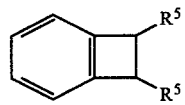

XIII wherein $R^5$ is as above.

The reaction of a compound of formula XI with a trans compound of formula XIII to give a compound of formula XII is suitably carried out in an inert organic solvent, especially an aromatic hydrocarbon such as benzene, toluene or xylene. It is preferred to carry out this reaction at an elevated temperature, conveniently at the reflux temperature of the reaction mixture. If desired, the reaction can be carried out under the atmosphere of an inert gas such as nitrogen or argon.

2 mols of the carboxylic acid $R^5H$ are then eliminated from a compound of formula XII by heating or treatment with a base, there being obtained a compound of formula IX. The heating of a compound of formula XII is preferably carried out in an inert organic solvent. Preferred among the solvents which can be used for this purpose are aromatic hydrocarbons such as benzene, toluene and xylene. The heating is preferably carried out at the reflux temperature of the mixture. If desired, the heating may be carried out under the atmosphere of an inert gas such as nitrogen or argon. Preferably, a compound of formula XII is heated in situ; that is to say, without isolation from the medium in which it is prepared. The treatment of a compound of formula XII with a base can be carried out using an inorganic base or an organic base. It is preferred to carry out this treatment using an inorganic base, particularly an alkali metal hydroxide such as sodium hydroxide or potassium hydroxide, in a lower alkanol (e.g. methanol or ethanol). This treatment is conveniently carried out at about room temperature.

The compounds of formula X hereinbefore can be prepared, in turn, from a cis/trans compound corresponding to formula X. Thus, such a cis/trans compound can be treated with an aromatic boronic acid to give a mixture of the cis boronic acid ester and unchanged trans diol. This mixture can be separated and the cis boronic acid ester can be converted into the cis diol. The treatment with an aromatic boronic acid such as one of those mentioned hereinbefore, preferably benzeneboronic acid, is expediently carried out in an inert organic solvent such as ethyl acetate at an elevated temperature, suitably at the reflux temperature of the mixture, and, if desired, under the atmosphere of an inert gas such as nitrogen or argon. The separation of the cis boronic acid ester and trans diol can be carried out by chromatography, suitably on silica gel. The cis boronic acid ester is conveniently converted into the cis diol by treatment with an acid, preferably a carboxylic acid such as acetic acid, in the presence of an excess of a 1,3-diol such as 2-methyl-2,4-pentanediol. The treatment is conveniently carried out in an inert organic solvent, preferably a halogenated hydrocarbon such as dichloromethane, and at room temperature.

A trans diol can be converted into a corresponding cis boronic acid ester which, in turn, can be converted into the cis diol. The conversion of the trans diol into the cis boronic acid ester can be carried out by treatment with an aromatic boronic acid such as one of those mentioned earlier, preferably benzeneboronic acid, in the presence of an organic sulphonic acid, preferably an aromatic sulphonic acid such as toluene-4-sulphonic acid. This treatment is advantageously carried out in an inert organic solvent, preferably an aromatic hydrocarbon such as benzene, at about room temperature. This cis boronic acid ester obtained can then be converted into the cis diol in the manner described earlier.

Alternatively, compounds of formula VIII hereinbefore can be prepared, for example, as shown in Formula Scheme II hereinafter in which $R^1$ and Ar have the significance given earlier.

Formula Scheme II

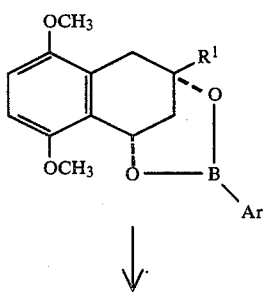

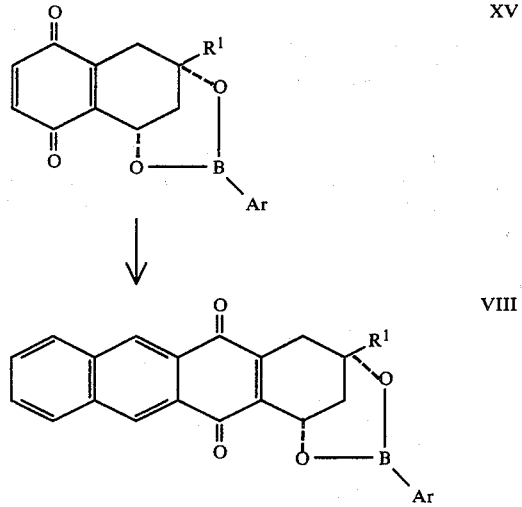

Having regard to Formula Scheme II, a compound of formula XIV, which can be prepared as described earlier from a cis/trans compound corresponding to formula X, is converted into a compound of formula XV by treatment with ammonium ceric nitrate. This treatment is advantageously carried out in a mixture of water and a water-miscible inert organic solvent such as acetonitrile or the like. The treatment is advantageously carried out at about room temperature.

A compound of formula XV is then converted into a compound of formula VIII by reaction with a trans compound of formula XIII hereinbefore. The reaction of a compound of formula XV with a trans compound of formula XIII to give a compound of formula XIII is suitably carried out in an inert organic solvent, especially an aromatic hydrocarbon such as benzene, toluene or xylene. It is preferred to carry out this reaction at an elevated temperature, conveniently at the reflux temperature of the reaction mixture. If desired, the reaction can be carried out under the atmosphere of an inert gas such as nitrogen or argon.

Cis/trans compounds corresponding to formula X hereinbefore in which $R^1$ represents a group of formula (a') wherein n stands for 1 can be prepared, for example, by reducing a compound of the formula

XVI wherein $R^{10}$ is an esterified carboxy group and $R^6$ and $R^7$ together are alkyl-enedithio,
in a manner known per se to give a compound of the formula

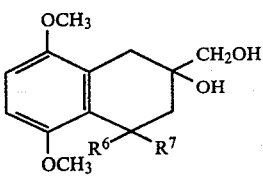

XVII wherein $R^6$ and $R^7$ are as above,
appropriately etherifying or acylating said compound of formula XVII, treating the resulting compound of the formula

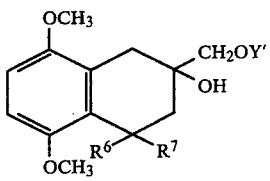

XVIII wherein $R^6, R^7$ and $Y'$ are as above,
with a mercuric salt and reducing the resulting compound of the formula

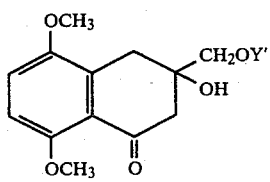

XIX wherein $Y'$ is as above.

The reduction of a compound of formula XVI can be carried out in a manner known per se; for example, using an alkali metal borohydride such as sodium borohydride in an inert organic solvent such as tetrahydrofuran etc.

The etherification of a compound of formula XVII can be carried out in a manner known per se; for example, with an alkyl halide (e.g. methyl iodide) in the presence of a base (e.g. sodium hydride) and in an inert organic solvent such as dioxan, tetrahydrofuran, 1,2-dimethoxyethane etc. The acylation of a compound of formula XVII can also be carried out in a manner known per se.

The treatment of a compound of formula XVIII with mercuric salt is preferably carried out using a mixture of mercuric chloride and mercuric oxide. This treatment is suitably carried out in a water-miscible inert organic solvent such as an alkanol (e.g. methanol, ethanol etc), tetrahydrofuran etc or in a mixture of such solvents which may also contain water. The treatment is preferably carried out at room temperature.

A compound of formula XIX is subsequently reduced in a manner known per se to give a desired cis/trans compound corresponding to formula X in which $R^1$ represents a group of formula (a') wherein n stands for 1. This reduction is conveniently carried out using an alkali metal borohydride, preferably sodium borohydride, in a customary inert organic solvent such as tetrahydrofuran. Conveniently, this reduction is carried out at room temperature. If desired, the reduction can be carried out under the atmosphere of an inert gas such as nitrogen or argon.

Cis/trans compounds corresponding to formula X in which $R^1$ represents a group of formula (a') wherein n stands for 2 can be prepared, for example, by first converting a compound of formula XVII into a compound of the formula

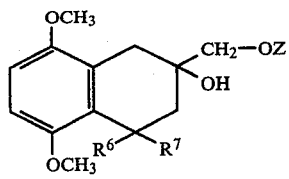

XX wherein $R^6$ and $R^7$ are as above and Z is a lower alkylsulphonyl or arylsulphonyl group.

This conversion can be carried out in a manner known per se; for example, by reaction with a lower alkylsulphonyl chloride (e.g. methanesulphonyl chloride) or, preferably, with an arylsulphonyl chloride (e.g. toluene-4-sulphonyl chloride) in the presence of an appropriate base (e.g. a tertiary amine such as pyridine, 4-dimethylaminopyridine etc) and at a low temperature (e.g. 0°–5° C.).

In the next step, a compound of formula XX is treated with an alkali metal cyanide to give a compound of the formula

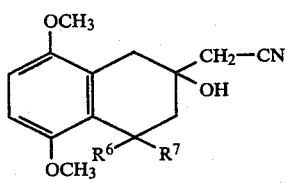

XXI wherein $R^6$ and $R^7$ are as above,
This treatment is carried out in a known manner; for example, using potassium cyanide in aqueous dimethyl sulphoxide or dimethylformamide. compound of the formula

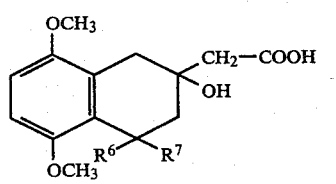

XXII wherein $R^6$ and $R^7$ is as above,
This hydrolysis is carried out in a manner known per se for the hydrolysis of nitriles to the corresponding acids; for example, using an alkali metal hydroxide such as potassium hydroxide in an aqueous lower alkanol such as aqueous ethanol.

A compound of formula XXII is then reduced to give a compound of the formula

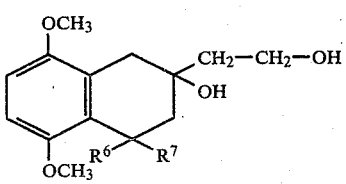

XXIII wherein $R^6$ and $R^7$ are as above.

This reduction can be carried out out in a manner known per se for the reduction of carboxylic acids to corresponding alcohols. Thus, for example, the reduction can be carried out using an alkali metal aluminium hydride (e.g. lithium aluminium hydride) in an inert organic solvent (e.g. tetrahydrofuran, dioxan etc). Again, for example, the reduction can be carried out using diborane. In certain circumstances it can be advantageous to convert a compound of formula XXII into an ester (e.g. the methyl ester) prior to the reduction.

Subsequently, a compound of formula XXIII is subjected to etherification or acylation as required, treatment with a mercuric salt and reduction in an analogous manner to that described earlier, there being thereby obtained a desired cis/trans compound corresponding to formula X in which $R^1$ represents a group of formula (a') wherein n stands for 2.

Cis/trans compounds corresponding to formula X in which $R^1$ represents a methyl group can be prepared, for example, by reducing a compound of formula XX with an alkali metal aluminium hydride such as lithium aluminium hydride in a known manner followed by treatment with a mercuric salt and reduction as described earlier. Cis/trans compounds corresponding to formula X in which $R^1$ represents a different lower alkyl group can be prepared similarly from corresponding ω-(lower alkylsulphonyloxy or arylsulphonyloxy)-(lower alkyl) compounds. For example, from a lower alkylsulphonate or arylsulphonate derived from a compound of formula XXIII there can be obtained a cis/-trans compound corresponding to formula X in which $R^1$ represents an ethyl group. Alternatively, this lower alkylsulphonate of arylsulphonate can be chain-lengthened according to the procedure described earlier (i.e. via a nitrile, acid and alcohol). This chain-lengthening can, of course, be repeated as required.

Alternatively, cis/trans compounds corresponding to formula X in which $R^1$ represents an ethyl group can be prepared, for example, as shown in Formula Scheme III hereinafter in which $R^6$, $R^7$, $R^{10}$ and Z have the significance given earlier.

Formula Scheme III

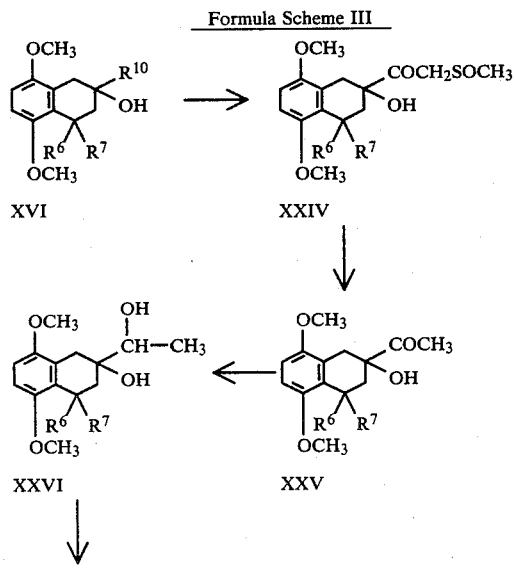

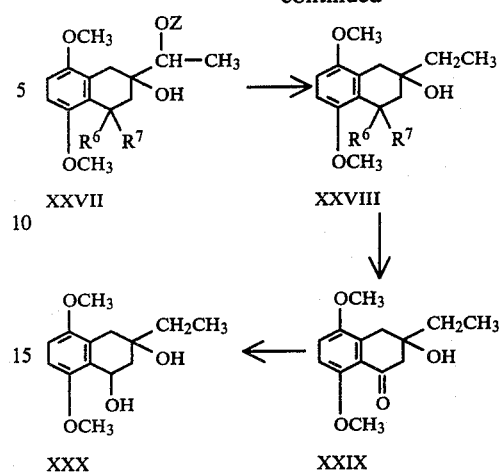

Having regard to Formula Scheme III, a compound of formula XVI is converted into a compound of formula XXIV by treatment with an alkali metal salt of dimethyl sulphoxide. This treatment is preferably carried out using the sodium salt of dimethyl sulphoxide and in an inert organic solvent (e.g. tetrahydrofuran) at about 0° C.

A compound of formula XXIV is then converted into a compound of formula XXV by treatment with aluminium amalgam. This treatment is suitably carried out in the presence of an inert solvent (e.g. aqueous tetrahydrofuran) at a temperature between about 10° C. and 20° C.

Subsequently, a compound of formula XXV is converted into a compound of formula XXVI by reduction in a manner known per se; for example, using an alkali metal borohydride such as sodium borohydride in an inert organic solvent such as tetrahydrofuran etc.

In the next step a compound of formula XXVI is converted into a compound of formula XXVII in a manner known per se; for example, by reaction with a lower alkylsulphonyl chloride (e.g. methanesulphonyl chloride) in the presence of an appropriate base (e.g. a tertiary amine such as pyridine) and at a low temperature (e.g. 0°–5° C.).

A compound of formula XXVII is then converted into a compound of formula XXVIII by reduction with an alkali metal aluminium hydride such as lithium aluminium hydride in a known manner.

A compound of formula XXVIII is subsequently converted into a compound of formula XXIX by treatment with a mercuric salt as described earlier in connection with the conversion of a compound of formula XVIII into a compound of formula XIX.

Finally, a compound of formula XXIX is converted into a cis/trans compound of formula XXX by reduction in a manner analogous to that described earlier in connection with the reduction of a compound of formula XIX.

The compounds of formula XVI hereinbefore can be prepared, for example, by first appropriately ketalising a compound of the formula

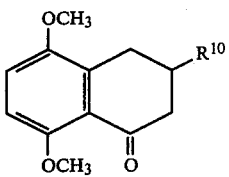

wherein $R^{10}$ is as above,
to give a compound of the formula

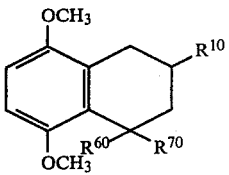

wherein $R^{10}$ is as above and $R^{60}$ and $R^{70}$ together are an alkylenedioxy group or an ethylenedioxy group. Ketalisation of a compound of formula XXXI, which is a known compound or an analogue of a known compound, can be carried out in a manner known per se for the ketalisation of an oxo group. For example, the ketalisation can be carried out using an appropriate alcohol in the presence of toluene-4-sulphonic acid and in the presence of a suitable inert organic solvent such as an aromatic hydrocarbon (e.g. benzene, toluene etc) at an elevated temperature (e.g. at the reflux temperature of the reaction mixture).

A compound of formula XXXII is then converted into a compound of the formula

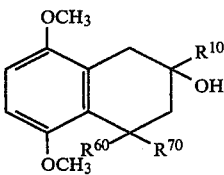

wherein $R^{10}, R^{60}$ and $R^{70}$ are as above.

A compound of formula XXXII is converted into a compound of formula XXXIII by first forming the lithium enolate of a compound of formula XXIII and then treating the enolate either with diperoxo-oxohexamethylphosphoramidomolybdenum (IV) pyridine ($MoO_5.py.HPMT$) or with oxygen in the presence of a trialkylphosphite.

The conversion of a compound of formula XXXII into a lithium enolate is carried out in a manner known per se; for example, using lithium diisopropylamide in an inert organic solvent such as tetrahydrofuran at a low temperature (e.g. $-78°$ C.).

The lithium enolate is then treated, preferably in situ, either with the diperoxo-oxohexamethylphosphoramidomolybdenum (VI) pyridine, suitably at a temperature between about room temperature and $-78°$ C., or with oxygen in the presence of a trialkylphosphite (e.g. triethylphospite), suitably by passing oxygen gas through a mixture of the enolate and the trialkylphosphite in an inert organic solvent such as tetrahydrofuran at a low temperature (e.g. $-78°$ C.).

A compound of formula XXXIII is then converted into a compound of formula XVI by replacing the alkylenedioxy group denoted by $R^{60}$ and $R^{70}$ together in a compound of formula XXXIII by an alkylenedithio group, especially the ethylenedithio group. This replacement can be carried out by treating the alkylenedioxy-substituted compound with an appropriate alkanedithiol (e.g. ethanedithiol) in the presence of boron trifluoride etherate. This treatment is suitably carried out in an inert organic solvent such as a halogenated hydrocarbon (e.g. dichloromethane) at a temperature of about 0° C.

The starting materials of formula III hereinbefore are known compounds or analogues of known compounds.

The compounds of formula I and their pharmaceutically acceptable acid addition salts possess antibiotic and antitumour activity.

The activity of the compounds of formula I and their pharmaceutically acceptable acid addition salts can be demonstrated using standard pharmacological tests. For example, the in vivo antitumour activity can be demonstrated using the following test:

The test was carried out using laboratory mice. The test substances were dissolved in water or, if insoluble, were suspended in propyleneglycol. Solutions and suspensions were used only for 2 days and were stored in the dark at 4° C. $10^5$ viable lymphocyte leukemia tumour cells were injected into mice and treatment was started the same day with five daily intraperitoneal injections of the test substance per week. Untreated control animals died between day 9 and day 12. The efficacy of the treatment is expressed as the quotient T/C which denotes the mean survival time of treated animals divided by the mean survival time of control animals. In this test (1S)-cis-1-[(3-amino-2,3,6-trideoxy-α-L-lyxohexopyranosyl)oxy]-1,2,3,4,6,11-hexahydro-3,5,12-trihydroxy-3-hydroxymethyl-6,11-dioxonaphthacene has a T/C of 2.31 at a dosage of 0.1 mg/kg i.p. and (1S)-cis-1-[(3-amino-2,3,6-trideoxy-α-L-lyxohexopyranosyl)oxy]-1,2,3,4,6,11-hexahydro-3,5,12-trihydroxy-3-methyl-6,11-dioxonaphthacene has a T/C of 4.0 at a dosage of 0.5 mg/kg i.p.

The compounds of formula I and their pharmaceutically acceptable acid addition salts can be used as medicaments; for example, in the form of pharmaceutical preparations which contain them in association with a compatible pharmaceutical carrier material. This carrier material can be an inert organic or inorganic carrier material suitable for enteral (e.g. oral) or parenteral administration. Examples of such carrier materials are water, gelatin, talc, starch, magnesium stearate, gum arabic, vegetable oils, polyalkyleneglycols, petroleum jelly and the like. The pharmaceutical preparations can be produced in a conventional manner and finished dosage forms can be solid dosage forms (e.g. tablets, dragéees, suppositories, capsules etc) or liquid dosage forms (e.g. solutions, suspensions, emulsions etc). The pharmaceutical preparations may be subjected to conventional pharmaceutical operations such as sterilisation and/or may contain conventional adjuvants such as preservatives, stabilisers, wetting agents, buffers, salts for varying the osmotic pressure etc. They may also contain other therapeutically valuable substances.

The compounds of formula I and their pharmaceutically acceptable acid salts may be administered to adults for the treatment of human malignant tumours using a continuous regimen (e.g. daily administration) or a periodic regimen (e.g. monthly administration). In general, the total dosage per treatment will be within the range of about 25 mg/m²–700 mg/m² (milligrams per square meter of skin area). It will, however, be appreciated that this dosage range is given by way of example only and that it can be varied upwards or downwards depending on factors such as the particular compound of formula I or salt being administered, the route of administration, the severity of the condition being treated and the requirements of the patient as determined by the attending physician.

The following Examples illustrate the process provided by the present invention:

EXAMPLE 1

(A) A solution of 1.0 g of (1S)-cis-3-acetoxymethyl-1,2,3,4,6,11-hexahydro-1,3,5,12-tetrahydroxy-6,11-dioxonaphthacene in 100 ml of tetrahydrofuran was cooled to −5° C. and 1.0 g of 2,3,6-trideoxy-4-O-p-nitrobenzoyl-3-trifluoroacetamido-α-L-lyxopyranosyl chloride was added. The mixture was stirred while a solution of 0.48 g of silver trifluoromethane-sulphonate in 15 ml of dry diethyl ether was added over a period of 20 minutes. After completion of the addition, a further 1.0 g of the aforementioned chlorosugar was added and then a further 0.48 g of silver trifluoromethanesulphonate in 15 ml of dry diethyl ether was added over a period of 20 minutes. The mixture was stirred at −5° C. for 0.5 hour, then poured into 300 ml of 10% potassium hydrogen carbonate solution and extracted with four 100 ml portions of dichloromethane. The dichloromethane extracts were dried over sodium sulphate and evaporated to give a red gum which was purified by column chromatography on silica gel using hexane/ethyl acetate (1:1, vol/vol) for the elution. In addition to 132 mg of unreacted dioxonaphthacene starting material, there were obtained 1.4 g of (1S)-cis-3-acetoxymethyl-1-[(2,3,6-trideoxy-3-trifluoroacetamido-4-O-p-nitrobenzoyl-α-L-lyxohexopyranosyl)oxy]-1,2,3,4,6,11-hexahydro-3,5,12-trihydroxy-6,11-dioxonaphthacene in the form of a red gum which was used without further purification.

(B) 1.4 g of (1S)-cis-3-acetoxymethyl-1-[(2,3,6-trideoxy-3-trifluoroacetamido-4-O-p-nitrobenzoyl-α-L-lyxohexopyranosyl)-oxy]-1,2,3,4,6,11-hexahydro-3,5,12-trihydroxy-6,11-dioxonaphthacene were dissolved in a mixture of 40 ml of dichloromethane and 100 ml of methanol and the resulting solution was cooled to 0° C. 0.1M aqueous sodium hydroxide solution was added dropwise to produce a permanent brown-purple colour. After 10 minutes, thin-layer chromatography indicated that no starting material remained. The reaction was quenched by the addition of acetic acid to produce an orange-red coloured solution. The mixture was diluted with 250 ml of water and extracted with four 100 ml portions of dichloromethane. The combined dichloromethane extracts were dried over sodium sulphate and evaporated to give an orange gum which was purified by column chromatography using acetone/dichloromethane (1:10 vol/vol) for the elution. Crystallisation from acetone/diethyl ether gave 0.9 g of (1S)-cis-3-acetoxy-methyl-1-[(2,3,6-trideoxy-3-trifluoroacetamido-α-L-lyxohexopyranosyl)oxy]-1,2,3,4,6,11-hexahydro-3,5,12-trihydroxy-6,11-dioxonaphthacene in the form of orange-red crystals of melting point 138°–141° C.; $[\alpha]_D^{20} = +170.3°$ (c=0.1% in chloroform).

(C) 0.8 g of (1S)-cis-3-acetoxymethyl-1-[(2,3,6-trideoxy-3-trifluoroacetamido-α-L-lyxohexopyranosyl)oxy]-1,2,3,4,6,11-hexahydro-3,5,12-trihydroxy-6,11-dioxonaphthacene was dissolved in a mixture of 100 ml of dichloromethane and 50 ml of methanol and the solution was cooled to 0° C. 0.1M aqueous sodium hydroxide was added to produce a deep purple colour. The solution was allowed to return to room temperature and was stirred for ca 2–2.5 hours until thin-layer chromatography showed that no starting material remained. The reaction was quenched by the addition of acetic acid to restore the orange-red colour, the resulting solution was diluted with 250 ml of water and extracted with four 100 ml portions of dichloromethane. The combined dichloromethane extracts were dried over sodium sulphate and evaporated to give an orange solid. Crystallisation from tetrahydrofuran/diethyl ether gave 0.65 g of (1S)-cis-1-[(2,3,6-trideoxy-3-trifluoroacetamido-α-L-lyxohexopyranosyl)oxy]-1,2,3,4,6,11-hexahydro-3,5,12-trihydroxy-3-hydroxymethyl-6,11-dioxonaphthacene in the form of orange-red crystals of melting point 239°–240° C.; $[\alpha]_D^{20} = +151.6°$ (c=0.1% in chloroform).

(D) 500 mg of (1S)-cis-1-[(2,3,6-trideoxy-3-trifluoroacetamido-α-L-lyxohexopyranosyl)oxy]-1,2,3,4,6,11-hexahydro-3,5,12-trihydroxy-3-hydroxymethyl-6,11-dioxonaphthacene were dissolved in 50 ml of 0.1M aqueous sodium hydroxide and the solution was stirred at room temperature for 45 minutes. The solution was adjusted to pH 8–9 by the addition of 0.1M aqueous hydrochloric acid and then repeatedly extracted with dichloromethane containing 10% ethanol until the extracts were virtually colourless. The combined extracts were washed with water, dried over sodium sulphate and evaporated to give a red solid. This solid was dissolved in 10 ml of dichloromethane containing 2 ml of methanol and filtered. 4 ml of 0.25M methanolic hydrogen chloride were added while swirling and the solution was concentrated to ca 5 ml. After precipitation by the addition of 50 ml of anhydrous diethyl ether, filtration, washing the filter residue with diethyl ether and drying in vacuo, there were obtained 455 mg of (1S)-cis-1-[(3-amino-2,3,6-trideoxy-α-L-lyxohexopyranosyl)oxy]-1,2,3,4,6,11-hexahydro-3,5,12-trihydroxy-3-hydroxymethyl-6,11-dioxonaphthacene hydrochloride in the form of an orange-red solid of melting point 183°–186° C. (decomposition); $[\alpha]_D^{20} = +153.2°$ (c=0.05% in methanol).

The (1S)-cis-3-acetoxymethyl-1,2,3,4,6,11-hexahydro-1,3,5,12-tetrahydroxy-6,11-dioxonaphthacene used as the starting material can be prepared as follows:

(a) A solution of 2 mmol of (1S)-cis-3-acetoxymethyl-1,2,3,4,5,12-hexahydro-5,12-dioxonaphthacene-1,3-diol and 244 mg (2 mmol) of benzeneboronic acid in a mixture of 150 ml of benzene and 0.5 ml of glacial acetic acid was stirred and heated under reflux for 1 hour. The mixture was left to cool and the solvent was removed by evaporation to give a yellow residue. This residue was triturated with 50 ml of diethyl ether and filtered to give (1S)-cis-3-acetoxymethyl-1,2,3,4,5,12-hexahydro-5,12-dioxo-1,3-naphthacenediyl benzeneboronate in the form of a yellow powder which was used without further purification.

(b) 1.78 mmol of (1S)-cis-3-acetoxymethyl-1,2,3,4,5,12-hexahydro-5,12-dioxo-1,3-naphthacenediyl benzeneboronate were dissolved in a mixture of 40 ml of dry pyridine and 20 ml of acetic anhydride. 10% palladium-on-carbon was added and the mixture was hydrogenated at room temperature and atmospheric pressure for 0.5 hour. The catalyst was removed by filtration and the filtrate was diluted with 160 ml of dichloromethane. The resulting solution was washed with three 200 ml portions of water, dried over anhydrous sodium sulphate, filtered and evaporated. The residue was triturated with diethyl ether and filtered to give 99% of (1S)-cis-5,12-diacetoxy-3-acetoxymethyl-1,2,3,4-tetrahydro-1,3-naphthacenediyl benzeneboronate in the form of pale yellow crystals of melting point 256°–258° C.; $[\alpha]_D^{20} = +251.3°$ (c=0.1% in dioxan).

(c) 0.6 mmol of (1S)-cis-5,12-diacetoxy-3-acetoxymethyl-1,2,3,4-tetrahydro-1,3-naphthacenediyl benzeneboronate were dissolved in a mixture of 18 ml of glacial acetic acid and 6 ml of acetic anhydride. 240 mg (2.4 mmol) of finely ground chromium trioxide were added and the mixture was stirred at room temperature for 16 hours. The mixture was then poured into 250 ml of water and the resulting suspension was extracted with two 200 ml portions of dichloromethane. The combined dichloromethane extracts were evaporated and the residue was triturated with diethyl ether and filtered to give (1S)-cis-5,12-diacetoxy-3-acetoxymethyl-1,2,3,4,6,11-hexahydro-6,11-dioxo-1,3-naphthacenediyl benzeneboronate in the form of pale yellow crystals of melting point 204°–205° C.; $[\alpha]_D^{20} = +180.3°$ (c=0.1% in dioxan).

(d) A solution of 0.17 mmol of (1S)-cis-5,12-diacetoxy-3-acetoxymethyl-1,2,3,4,6,11-hexahydro-6,11-dioxo-1,3-naphthacenediyl benzeneboronate in 20 ml of dichloromethane was stirred and cooled to −78° C. A solution of 125 mg of boron trichloride in 5 ml of dichloromethane was added and the mixture was stirred and left to warm to −10° C. over a period of 1 hour. The mixture was then poured into 20 ml of ice-cold 2-M hydrochloric acid and the layers were separated. The organic layer was washed with 20 ml of water, dried over anhydrous sodium sulphate, filtered and the filtrate was evaporated. The residue was triturated with 5 ml of diethyl ether and filtered to give (1S)-cis-3-acetoxymethyl-1,2,3,4,6,11-hexahydro-5,12-dihydroxy-6,11-dioxo-1,3-naphthacenediyl benzeneboronate in the form of a red semi-solid which was used without further purification.

(e) 0.10 mmol of (1S)-cis-3-acetoxymethyl-1,2,3,4,6,11-hexahydro-5,12-dihydroxy-6,11-dioxo-1,3-naphthacenediyl benzeneboronate were dissolved in 6 ml of dichloromethane. 1.5 ml of 2-methyl-2,4-pentanediol and 0.25 ml of glacial acetic acid were added and the resulting solution was stirred at room temperature for 40 hours. The solution was then washed with three 15 ml portions of water, dried over anhydrous sodium sulphate, filtered and the solvent was removed by evaporation. The oily crystalline residue was triturated with diethyl ether and filtered to give (1S)-cis-3-acetoxymethyl-1,2,3,4,6,11-hexahydro-1,3,5,12-tetrahydroxy-6,11-dioxonaphthacene which, after purification by chromatography on silica gel using 5% methanol in toluene, formed red crystals of melting point 201°–203° C.; $[\alpha]_D^{20} = +119.8°$ (c=0.1% in dioxan).

The (1S)-cis-3-acetoxymethyl-1,2,3,4,5,12-hexahydro-5,12-dioxonaphthacene-1,3-diol used in paragraph (a) of of this Example can be prepared as follows:

(i) 40 g of methyl rac-1,2,3,4-tetrahydro-5,8-dimethoxy-4-oxonaphthalene-2-carboxylate were added to a mixture of 800 ml of toluene, 800 ml of hexane, 30 ml of ethyleneglycol and 0.65 g of toluene-4-sulphonic acid. The mixture was heated under reflux for 24 hours using a Dean-Stark trap. The solution was cooled in an ice-bath and washed with three 124 ml portions of 10% potassium hydrogen carbonate solution and 200 ml of brine, dried and the solvent was evaporated. The residue was taken up in 200 ml of methanol at 70° C. and 0.5 g of a 50% dispersion of sodium hydride in mineral oil was added. The solution obtained was left to cool to room temperature and then cooled further in an ice-bath for 2 hours. The crystalline product was filtered off, washed with cold methanol and dried in vacuo. There were obtained 28.5 g (61%) of methyl rac-4,4-ethylenedioxy-1,2,3,4-tetrahydro-5,8-dimethoxynaphthalene-2-carboxylate in the form of colourless crystals of melting point 133°–134° C.

(ii)(a) To a solution of 84 ml of diisopropylamine in 250 ml of dry tetrahydrofuran at −78° C. under argon were added 39 ml of a 1.6 molar solution of n-butyl lithium in hexane. The mixture was stirred for 10 minutes and then a solution of 12.32 g of methyl 4,4-ethylenedioxy-1,2,3,4-tetrahydro-5,8-dimethoxynaphthalene-2-carboxylate in 75 ml of dry tetrahydrofuran was added rapidly. The mixture was held at −78° C. while stirring for 50 minutes and then 27.8 g of finely ground diperoxo-oxohexamethylphosphoramidomolybdenum (VI) pyridine were added. After a further 80 minutes, the mixture was warmed to 0° C. and stirred for 20 minutes before the addition of 400 ml of water. After 10 minutes, most of the tetrahydrofuran was evaporated in vacuo and the aqueous residue was extracted with five 200 ml portions of ethyl acetate. The combined ethyl acetate extracts were dried over magnesium sulphate, filtered and evaporated to give an oil which was purified by chromatography on silica gel using ethyl acetate/hexane (1:1, vol/vol) for the elution. After the elution of 1.57 g of starting material, there were obtained 7.51 g (58%) of methyl rac-4,4-ethylenedioxy-1,2,3,4-tetrahydro-2-hydroxy-5,8-dimethoxynaphthalene-2-carboxylate in the form of colourless crystals of melting point 74°–75° C.

(ii)(b) A solution of the lithium enolate of methyl rac-4,4-ethylenedioxy-1,2,3,4-tetrahydro-5,8-dimethoxy-naphthalene-2-carboxylate was prepared in tetrahydrofuran as described in part (ii)(a) hereinbefore from 9.84 g of methyl rac-4,4-ethylenedioxy-1,2,3,4-tetrahydro-5,8-dimethoxynaphthalene-2-carboxylate. The enolate was added over a period of 5 minutes at −78° C. to a stirred solution of 11.2 ml of dry triethylphosphite in 60 ml of tetrahydrofuran through which a rapid stream of oxygen was passing. The passage of oxygen was maintained for 50 minutes and the temperature was held at −78° C. The reaction was then quenched by the addition of 8.8 ml of acetic acid. The cooling bath was removed and, after 5 minutes, 200 ml of water were added. After a further 20 minutes, most of the tetrahydrofuran was evaporated and the product was extracted into four 100 ml portions of ethyl acetate. The combined ethyl acetate extracts were washed with 200 ml of 10% aqueous potassium hydrogen carbonate, dried over magnesium sulphate, filtered and evaporated to give a yellow oil which was dissolved in 130 ml of ether and left to crystallise. There were obtained 6.86 g (66%) of methyl rac-4,4-ethylenedioxy-1,2,3,4-tetrahydro-2-hydroxy-5,8-dimethoxynaphthalene-2-carboxylate in the form of colourless crystals of melting point 74°–75° C.

(iii) 10 g of methyl rac-4,4-ethylenedioxy-1,2,3,4-tetrahydro-2-hydroxy-5,8-dimethoxynaphthalene-2-carboxylate were dissolved in 30 ml of dichloromethane and the solution was cooled to 0° C. To the solution were added 4 ml of ethanedithiol followed by 4 ml of boron trifluoride etherate. The mixture was stirred at 0° C. for 15 minutes and then poured into 200 ml of diethyl ether. The organic layer was washed with three 50 ml portions of 5% sodium hydroxide solution and evaporated to give a yellow oil which was taken up in 200 ml of methanol. 100 ml of 5% sodium hydroxide solution were added and the resulting solution was stirred at room temperature for 1.5 hours. Most of the methanol was then evaporated, the residue was diluted with 250 ml of water and washed with three 100 ml portions of ether. The aqueous layer was acidified with hydrochloric acid and the precipitated oil was left to solidfy. The product was collected by filtration, washed free from acid using water and dried. The crude acid was purified by suspension in 150 ml of ethyl acetate and heating under reflux for 30 minutes. The mixture was cooled and the product was collected by filtration after 24 hours. There were obtained 7.0 g (66.5%) of 1',2',3',4'-tetrahydro-2'-hydroxy-5',8'-dimethoxyspiro[1,3-dithiolane-2,4'-naphthalene]-2'-carboxylic acid in the form of colourless crystals of melting point 189°–189.5° C.

(iv) A suspension of 3.42 g of rac-1',2',3',4'-tetrahydro-2'-hydroxy-5',8'-dimethoxyspiro[1,3-dithiolane-2,4'-naphthalene]-2'-carboxylic acid in 168 ml of ethyl acetate and 4.0 g of brucine was heated under reflux until a clear solution was obtained. After seeding, the solution was left to cool slowly to room temperature. The crystalline precipitate (3.6 g) was collected after 2 days. The precipitate was dissolved in 1500 ml of boiling ethyl acetate, the solution was concentrated to 600 ml and left to cool slowly. The crystalline product [2.7 g $[\alpha]_D^{20} = -46.6°$, c=0.5% in dimethylformamide] was suspended in 150 ml of ethyl acetate and shaken with three 10 ml portions of 5-M hydrochloric acid and with two 100 ml portions of brine. After drying over magnesium sulphate, the solvent was evaporated to give a colourless oil which was crystallised from diethyl ether to yield 1.22 g of (R)-1',2',3',4'-tetrahydro-2'-hydroxy-5',8'-dimethoxyspiro[1,3-dithiolane-2,4'-naphthalene]-2'-carboxylic acid in the form of colourless crystals of melting point 147°–149° C.; $[\alpha]_D^{20} = +13.8°$ (c=0.5% in dioxan).

(v) The ethyl acetate mother liquors from the first crystallisation of the procedure described in the preceding paragraph were shaken with three 10 ml portions of 5-M hydrochloric acid and with two 100 ml portions of brine, dried and evaporated to give 1.7 g of a solid residue. This residue was suspended in 50 ml of ethyl acetate and heated under reflux for 0.5 hour. After cooling, 0.6 g of rac-1',2',3'-tetrahydro-2'-hydroxy-5',8'-dimethoxyspiro[1,3-dithiolane-2,4'-naphthalene]-2'-carboxylic acid of melting point 189°–190° C. was obtained. The mother liquors were evaporated and the residue was taken up in diethyl ether, filtered, and the product crystallised to give 1.12 g of (S)-1',2',3',4'-tetrahydro-2'-hydroxy-5',8'-dimethoxyspiro[1,3-dithiolane-2,4'-naphthalene]-2'-carboxylic acid in the form of colourless crystals of melting point 145°–148° C.; $[\alpha]^{20} = -13.5°$ (c=0.5% in dioxan).

(vi) 20 g of (S)-1',2',3',4'-tetrahydro-2'-hydroxy-5',8'-dimethoxyspiro[1,3-dithiolane-2,4'-naphthalene]-2'-carboxylic acid were suspended in 200 ml of methanol and 40 ml of boron trifluoride/methanol were added. The mixture was stirred at room temperature for 3.5 hours to give a clear solution. Approximately 80 ml of methanol were removed by evaporation and the remaining solution was poured into 400 ml of dichloromethane. The organic solution was washed with 500 ml of water, 200 ml of 10% potassium hydrogen carbonate solution and 200 ml of brine. After drying over magnesium sulphate, the solvent was removed to give 24 g of a yellow gum. Crystallisation of this gum from diethyl ether/hexane gave 19.5 g (95.5%) of methyl (S)-1',2',3',4'-tetrahydro-2'-hydroxy-5',8'-dimethoxyspiro[1,3-dithiolane-2,4'-naphthalene]-2'-carboxylate in the form of colourless crystals of melting point 115°–117° C.; $[\alpha]_D^{20} = -12.7°$ (c=0.5% in chloroform).

(vii) 2.0 g of methyl (S)-1',2',3',4'-tetrahydro-2'-hydroxy-5',8'-dimethoxyspiro[1,3-dithiolane-2,4'-naphthalene]-2'-carboxylate were dissolved in 200 ml of dry tetrahydrofuran and 2.0 g of sodium borohydride were added to the solution. The resulting mixture was stirred at room temperature under nitrogen for 20 hours. The solvent was removed by evaporation and 100 ml of 10% ammonium chloride solution were added. The mixture was extracted with three 30 ml portions of ethyl acetate. The extracts were dried and evaporated to give (S)-1',2',3',4'-tetrahydro-3'-hydroxy-3'-hydroxymethyl-5',8'-dimethoxyspiro[1,3-dithiolane-2,1'-naphthalene] in the form of a colourless gum which was used directly in the next step.

(viii) 1.6 g of (S)-1',2',3',4'-tetrahydro-3'-hydoxy-3'-hydroxymethyl-5',8'-dimethoxyspiro[1,3-dithiolane-2,1'-naphthalene] were dissolved in 30 ml of dry pyridine and 1.5 g of acetic anhydride were added to the solution. The mixture was left to stand at room temperature for 20 hours and then poured into ice-cold 5-M sulphuric acid. The resulting mixture was extracted with ethyl acetate, the extracts were washed with water and sodium hydrogen carbonate solution, dried and evaporated to give (S)-3'-acetoxymethyl-1',2',3',4'-tetrahydro-3'-hydroxy-5',8'-dimethoxyspiro[1,3-dithiolane-2,1'-naphthalene] in the form of a colourless oil which was used directly in the next step.

(ix) 1.9 g of (S)-3'-acetoxymethyl-1',2',3',4'-tetrahydro-3'-hydroxy-5',8'-dimethoxyspiro[1,3-dithiolane-2,1'-naphthalene] in 40 ml of tetrahydrofuran were added to a stirred suspension of 6.4 g of mercuric chloride and 6.4 g of mercuric oxide in 200 ml of methanol containing 18 ml of water. After standing at room temperature for 1 hour, ca 150 ml of solvent were removed by evaporation under reduced pressure, 200 ml of dichloromethane were added and the resulting suspension was filtered to remove insoluble material. The filtrate was washed with three 200 ml portions of water, dried over magnesium sulphate and evaporated to give a solid residue. Trituration with diethyl ether gave (S)-3-acetoxymethyl-1,2,3,4-tetrahydro-3-hydroxy-5,8-dimethoxy-1-oxo-naphthalene in the form of an off-white powder which was used in the next step without purification.

(x) 2.37 g of the foregoing ketone were dissolved in 100 ml of tetrahydrofuran and 2.0 g of sodium borohydride were added. After stirring at room temperature for 2 hours, the solvent was removed by evaporation and 100 ml of 10% ammonium chloride were added. The mixture was extracted with three 100 ml portions of ethyl acetate, the extracts were dried over magnesium sulphate and evaporated to give a colourless gum. This gum was dissolved in 200 ml of ethyl acetate and 2.0 g of benzeneboronic acid and 3 drops of acetic acid were added. The mixture was heated under reflux for 1 hour, the solvent was removed by evaporation and 200 ml of toluene were added. After the addition of 75 mg of toluene-4-sulphonic acid, the solution was stirred at room temperature for 4.5 hours. The solution was washed with 50 ml of 10% potassium hydrogen carbonate solution, dried over magnesium sulphate and evaporated to give crude (S)-3-acetoxymethyl-1,2,3,4-tetrahydro-5,8-dimethoxynaphthalene-1,3-diyl benzeneboronate in the form of a semi-solid residue. This residue was dissolved in dichloromethane containing a small amount of acetic acid. 2-Methyl-2,4-pentanediol was added and the resulting solution was left to stand at room temperature for 24 hours. The mixture was poured into 5% potassium hydrogen carbonate solution and extracted with three portions of dichloromethane. The combined extracts were dried over magnesium sulphate an evaporated to give a colourless oil which was dissolved in hexane. The product was allowed to crystallise at 4° C. overnight. Filtration gave (S)-cis-3-acetoxymethyl-1,2,3,4-tetrahydro-5,8-dimethoxynaphthalene-1,3-diol in the form of colourless crystals of melting point 97°–98° C., $[\alpha]_D^{20} = -2.6°$ (c=0.5% in chloroform).

(xi) A solution of 1.1 g of ammonium ceric nitrate in 20 ml of water was added to a stirred solution of 296 mg of (S)-cis-3-acetoxymethyl-1,2,3,4-tetrahydro-5,8-dimethoxynaphthalene-1,3-diol in 20 ml of acetonitrile. After stirring at room temperature for 5 minutes, the mixture was poured into 200 ml of water and extracted with six 50 ml portions of dichloromethane. The combined organic extracts were dried over magnesium sulphate and evaporated to give (S)-cis-3-acetoxymethyl-1,2,3,4,5,8-hexahydro-5,8-dioxo-naphthalene-1,3-diol which was dissolved in 20 ml of xylene.

(xii) The solution obtained according to the preceding paragraph was treated with 0.3 g of trans-1,2-diacetoxy-1,2-dihydrobenzocyclobutene and the mixture was heated at 140° C. for 2 hours. After cooling, the solution was filtered through silica gel and the solvent was removed by evaporation to give a solid yellow residue. Trituration with ethyl acetate/diethyl ether gave 220 mg (60%) of (1S)-cis-3-acetoxymethyl-1,2,3,4,5,12-hexahydro-5,12-dioxonaphthacene-1,3-diol in the form of yellow crystals of melting point 189°–191° C.; $[\alpha]_D^{20} = +40.3°$ (c=0.5% in chloroform).

EXAMPLE 2

(A) In a manner analogous to that described in Example 1(A); from (1S)-cis-1,2,3,4,6,11-hexahydro-1,3,5,12-tetrahydroxy-3-methyl-6,11-dioxonaphthacene there was obtained, after crystallisation from tetrahydrofuran/hexane, (1S)-cis-1-[(2,3,6-trideoxy-3-trifluoroacetamido-4-O-p-nitrobenzoyl-α-L-lyxohexopyranosyl)oxy]-1,2,3,4,6,11-hexahydro-3,5,12-trihydroxy-3-methyl-6,11-dioxonaphthacene in the form of orange-red crystals of melting point 225°–226° C.; $[\alpha]_D^{20} = -101.8°$ (c=0.1% in chloroform).

(B) The product obtained according to the preceding paragraph was treated according to the procedure described in Example 1(B) to give (1S)-cis-1-[(2,3,6-trideoxy-3-trifluoroacetamido-α-L-lyxohexopyranosyl)oxy]-1,2,3,4,6,11-hexahydro-3,5,12-trihydroxy-3-methyl-6,11-dioxonaphthacene in the form of orange-red crystals of melting point 253°–254° C.; $[\alpha]_D^{20} = +180.9°$ (c=0.1% in chloroform).

(C) The product obtained according to the preceding paragraph was treated according to the procedure described in Example 1(D) to give (1S)-cis-1-[(3-amino-2,3,6-trideoxy-α-L-lyxohexopyranosyl)oxy]-1,2,3,4,6,11-hexahydro-3,5,12-trihydroxy-3-methyl-6,11-dioxonaphthacene hydrochloride in the form of orange-red crystals of melting point 174°–176° C. (decomposition); $[\alpha]_D^{20} = +160.1°$ (c=0.05% in methanol).

The (1S)-cis-1,2,3,4,6,11-hexahydro-1,3,5,12-tetrahydroxy-3-methyl-6,11-dioxonaphthacene used as the starting material can be prepared as follows:

(a) In a manner analogous to that described in Example 1(a), from (1S)-cis-1,2,3,4,5,12-hexahydro-3-methyl-5,12-dioxonaphthacene-1,3-diol there was obtained (1S)-cis-1,2,3,4,5,12-hexahydro-3-methyl-5,12-dioxo-1,3-naphthacenediyl benzeneboronate which was used in the next step without purification.

(b) In a manner analogous to that described in Example 1(b), from (1S)-cis-1,2,3,4,5,12-hexahydro-3-methyl-5,12-dioxo-1,3-naphthacenediyl benzeneboronate there was obtained (1S)-cis-5,12-diacetoxy-1,2,3,4-tetrahydro-3-methyl-1,3-naphthacenediyl benzeneboronate which was used in the next step without purification.

(c) Oxidation of (1S)-cis-5,12-diacetoxy-1,2,3,4-tetrahyro-3-methyl-1,3-naphthacenediyl benzeneboronate in a manner analogous to that described in Example 1(c) gave (1S)-cis-5,12-diacetoxy-1,2,3,4,6,11-hexahydro-3-methyl-6,11-dioxo-1,3-naphthacenediyl benzeneboronate which was used in the next step without purification.

(d) Treatment of (1S)-cis-5,12-diacetoxy-1,2,3,4,6,11-hexahydro-3-methyl-6,11-dioxo-1,3-naphthacenediyl benzeneboronate with boron trichloride in a manner analogous to that described in Example 1(d) gave (1S)-cis-1,2,3,4,6,11-hexahydro-5,12-dihydroxy-3-methyl-6,11-dioxo-1,3-naphthacenediyl benzeneboronate which was used in the next step without purification.

(e) In a manner analogous to that described in Example 1(e), from (1S)-cis-1,2,3,4,6,11-hexahydro-5,12-dihydroxy-3-methyl-6,11-dioxo-1,3-naphthacenediyl benzeneboronate there was obtained (1S)-cis-1,2,3,4,6,11-hexahydro-1,3,5,12-tetrahydroxy-3-methyl-6,11-dioxonaphthacene. Purification by column chromatography on silica gel using 5% methanol in toluene for the elution gave red crystals of melting point 214°–215° C.; $[\alpha]_D^{20} = +152.5°$ (c=0.1% in dioxan).

The (1S)-cis-1,2,3,4,5,12-hexahydro-3-methyl-5,12-dioxonaphthacene-1,3-diol used as the starting material in paragraph (a) of this Example can be prepared as follows:

(i) 326 mg of (S)-1',2',3',4'-tetrahydro-3'-hydroxy-3'-hydroxymethyl-5',8'-dimethoxyspiro[1,3-dithiolane-2,1'-naphthalene], prepared as described in Example 1(vii), were dissolved in 10 ml of pyridine and the solution was cooled to 0° C. 400 mg of toluene-4-sulphonyl chloride were added and the mixture was held at 4° C. for 20 hours. The solution was poured on to crushed ice, acidified with 5-M sulphuric acid and extracted with ethyl acetate. The ethyl acetate extract was washed with water and then with 5% potassium hydrogen carbonate solution. After drying, the solvent was removed by evaporation to give a white solid. Trituration of this solid with diethyl ether gave (S)-1',2',3',4'-tetrahydro-3'-hydroxy-5',8'-dimethoxyspiro[1,3-dithiolane-2,1'-naphthyl]-3'-methyl p-toluenesulphonate in the form of colourless crystals of melting point above 115° C. (decomposition); $[\alpha]_D^{20} = -37.5°$ (c=0.5% in chloroform).

(ii) 200 mg of (S)-1',2',3',4'-tetrahydro-3'-hydroxy-5',8'-dimethoxyspiro[1,3-dithiolane-2,1'-naphthyl]-3'-methyl p-toluenesulphonate were dissolved in 20 ml of dry tetrahydrofuran containing 100 mg of lithium aluminium hydride. The mixture was heated under reflux for 3.5 hours under a nitrogen atmosphere. The solution was cooled and quenched by the addition of saturated ammonium chloride solution. The solvent was removed by evaporation and the residue was taken up in dilute hydrochloric acid. The solution was extracted with ethyl acetate and the extracts were washed with water, dried and evaporated to give a colourless oil which crystallised from diethyl ether. There was obtained (S)-1′,2′,3′,4′-tetrahydro-3′-hydroxy-3′-methyl-5′,8′-dimethoxyspiro[1,3-dithiolane-2,1′-naphthalene] in the form of colourless crystals of melting point 152°–153° C.; $[\alpha]_D^{20} = -48.0°$ (c=0.5% in chloroform).

(iii) The foregoing compound was treated sequentially according to the procedures described in Example 1(ix) and (x), without purification of the products obtained, to give (S)-cis-1,2,3,4-tetrahydro-3-methyl-5,8-dimethoxynaphthalene-1,3-diol in the form of colourless crystals of melting point 166°–167° C.; $[\alpha]_D^{20} = -7.8°$ (c=0.5% in chloroform).

(iv) The foregoing diol was treated in a manner analogous to that described in Example 1(xi) and 1(xii) to give (1S)-cis-1,2,3,4,5,12-hexahydro-3-methyl-5,12-dioxonaphthacene-1,3-diol in the form of yellow crystals of melting point 209°–211° C.; $[\alpha]_D^{20} = +52.6°$ (c=0.5% in chloroform).

EXAMPLE 3

(A) 1.0 g of (1S)-cis-1,2,3,4,6,11-hexahydro-1,3,5,12-tetrahydroxy-3-methyl-6,11-dioxonaphthacene, prepared as described in Example 2(e), was dissolved in 100 ml of tetrahydrofuran and the solution was cooled to −5° C. A solution of 1.0 g of 2,3,6-trideoxy-4-O-p-nitrobenzoyl-3-trifluoroacetamido-α-L-arabinohexopyranosyl chloride in 30 ml of dichloromethane was added. The mixture was stirred while a solution of 0.48 g of silver trifluoromethanesulphonate in 15 ml of dry diethyl ether was added over a period of 20 minutes. After completion of the addition, a further 0.5 g of the aforementioned chlorosugar was added, followed by a further 0.24 g of silver trifluoromethanesulphonate in 7.5 ml of dry diethyl ether. The mixture was stirred at −5° C. for 0.5 hour, then poured into 300 ml of 10% potassium hydrogen carbonate solution and extracted with four 100 ml portions of dichloromethane. The dichloromethane extracts were dried over sodium sulphate and evaporated to give a red gum which was purified by column chromatography on silica gel using hexane/ethyl acetate (1:1, vol/vol) for the elution. In addition to 120 mg of unreacted dioxonaphthacene starting material, there were obtained 1.05 g of (1S)-cis-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-3-methyl-6,11-dioxonaphthacene in the form of orange-red crystals of melting point 244°–247° C. after crystallisation of enriched fractions from acetone/diethyl ether; $[\alpha]_D^{20} = +273.8°$ (c=0.1% in chloroform).

(B) 0.85 g of (1S)-cis-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-3-methyl-6,11-dioxonaphthacene was dissolved in a mixture of 50 ml of dichloromethane and 100 ml of methanol and the solution was cooled to 0° C. 0.1M aqueous sodium hydroxide was added dropwise to produce a brown-purple colour. After 30 minutes, thin-layer chromatography indicated that no starting material was present. The reaction was quenched by the addition of acetic acid to restore the orange colour. The mixture was diluted with 250 ml of water and extracted with four 100 ml portions of dichloromethane. The combined dichloromethane extracts were dried over sodium sulphate and evaporated to give an orange gum. Crystallisation of this gum from acetone/diethyl ether yielded (1S)-cis-1-[(2,3,6-trideoxy-3-trifluoroacetamido-α-L-arabinohexopyranosyl)oxy]-1,2,3,4,6,11-hexahydro-3,5,12-trihydroxy-3-methyl-6,11-dioxonaphthacene in the form of orange-red crystals of melting point 268°–269° C.; $[\alpha]_D^{20} = +197.5°$ (c=0.05% in chloroform).

(C) 565 mg of (1S)-cis-1-[(2,3,6-trideoxy-3-trifluoroacetamido-α-L-arabinohexopyranosyl)oxy]-1,2,3,4,6,11-hexahydro-3,5,12-trihydroxy-3-methyl-6,11-dioxonaphthacene were dissolved in 50 ml of acetone and the solution was added to 60 ml of 0.1M aqueous sodium hydroxide. After stirring at room temperature for 45 minutes, the pH of the solution was adjusted to about 8.5 by adding 0.1M aqueous hydrochloric acid. The solution was repeatedly extracted with dichloromethane containing 10% ethanol until the extracts were virtually colourless. The combined extracts were washed with water, dried over sodium sulphate and evaporated to give a red oil. This oil was dissolved in 12 ml of dichloromethane and 3 ml of methanol and filtered. 4 ml of 0.25M methanolic hydrogen chloride were added while swirling and the solution was concentrated to 8 ml. After precipitation with 75 ml of dry diethyl ether, filtration, washing the filter residue with dry diethyl ether and drying in vacuo, there were obtained 453 mg of (1S)-cis-1-[(3-amino-2,3,6-trideoxy-α-L-arabinohexopyranosyl)oxy]-1,2,3,4,6,11-hexahydro-3,5,12-trihydroxy-3-methyl-6,11-dioxonaphthacene hydrochloride in the form of an orange-red powder of melting point 181°–183° C. (decomposition); $[\alpha]_D^{20} = +242.6°$ (c=0.5% in methanol).

EXAMPLE 4

(A) In a manner analogous to that described in Example 3(A), from (1S)-cis-3-acetoxymethyl-1,2,3,4,6,11-hexahydro-1,3,5,12-tetrahydroxy-6,11-dioxonaphthacene there was obtained, after crystallisation from acetone/diethyl ether, (1S)-cis-3-acetoxymethyl-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-6,11-dioxonaphthacene in the form of orange-red crystals of melting point 262°–263° C.; $[\alpha]_D^{20} = +266.9°$ (c=0.1% in chloroform).

(B) The product obtained according to the preceding paragraph was treated according to the procedure described in Example 3(B) except that purification was carried out by column chromatography on silica gel using ethyl acetate/hexane (1:1 vol/vol) for the elution. After crystallisation of enriched fractions from acetone/diethyl ether, there was obtained (1S)-cis-3-acetoxymethyl-1-[(2,3,6-trideoxy-3-trifluoroacetamido-α-L-arabinohexopyranosyl)oxy]-1,2,3,4,6,11-hexahydro-3,5,12-trihydroxy-6,11-dioxonaphthacene in the form of orange-red crystals of melting point 242°–243° C.; $[\alpha]_D^{20} = +193.7°$ (c=0.1% in chloroform).

(C) 0.8 g of the product obtained according to the preceding paragraph was dissolved in a mixture of 100 ml of dichloromethane and 100 ml of methanol. 0.1M aqueous sodium hydroxide was added to produce a deep purple colour. The solution was stirred for 5.5 hours at room temperature and the reaction was then quenched by adding acetic acid to restore the orange-red colour. The resulting solution was diluted with 250 ml of water and extracted with four 100 ml portions of dichloromethane. The combined extracts were dried over sodium sulphate and evaporated to give an orange solid. Crystallisation of this solid from acetone/diethyl ether gave 0.63 g of (1S)-cis-1-[(2,3,6-trideoxy-3-trifluoroacetamido-α-L-arabinohexopyranosyl)oxy]-1,2,3,4,6,11-hexahydro-3,5,12-trihydroxy-3-hydroxymethyl-6,11-dioxonaphthacene in the form of orange-red crystals of melting point 237°–239° C.; $[α]_D^{20} = +236.9°$ (c=0.1% in acetone).

(D) The product obtained according to the preceding paragraph was treated in a manner analogous to that described in Example 3(C) to give (1S)-cis-1-[(3-amino-2,3,6-trideoxy-α-L-arabinohexopyranosyl)oxy]-1,2,3,4,6,11-hexahydro-3,5,12-trihydroxy-3-hydroxymethyl-6,11-dioxonaphthacene hydrochloride in the form of an orange power of melting point 189°–193° C. (decomposition); $[α]_D^{20} = +215.8°$ (c=0.05% in methanol).

EXAMPLE 5

(A) In a manner analogous to that described in Example 1(A), from (1S)-cis-3-ethyl-1,2,3,4,6,11-hexahydro-1,3,5,12-tetrahydroxy-6,11-dioxonaphthacene there was obtained, after crystallisation from ethyl acetate/petroleum ether (60°–80° C.), (1S)-cis-1-[(2,3,6-trideoxy-3-trifluoroacetamido-4-O-p-nitrobenzoyl-α-L-lyxohexopyranosyl)oxy]-3-ethyl-1,2,3,4,6,11-hexahydro-3,5,12-trihydroxy-6,11-dioxonaphthacene in the form of red crystals of melting point 181.5°–182.5° C.; $[α]_D^{20} = -98.4°$ (c=0.1% in dioxan).

(B) The product obtained according to the preceding paragraph was treated according to the procedure described in Example 1(B) to give (1S)-cis-1-[(2,3,6-trideoxy-3-trifluoroacetamido-α-L-lyxohexopyranosyl)oxy]-3-ethyl-1,2,3,4,6,11-hexahydro-3,5,12-trihydroxy-6,11-dioxonaphthacene in the form of orange crystals of melting point 241°–243° C.; $[α]_D^{20} = +188.6°$ (c=0.1% in dioxan).

(C) The product obtained according to the preceding paragraph was treated according to the procedure described in Example 1(D) to give (1S)-cis-1-[(3-amino-2,3,6-trideoxy-α-L-lyxohexopyranosyl)oxy]-3-ethyl-1,2,3,4,6,11-hexahydro-3,5,12-trihydroxy-6,11-dioxonaphthacene hydrochloride in the form of orange-red crystals of melting point 174°–176° C.; $[α]_D^{20} = +175.8°$ (c=0.1% in methanol).

The (1S)-cis-3-ethyl-1,2,3,4,6,11-hexahydro-1,3,5,12-tetrahydroxy-6,11-dioxonaphthacene used as the starting material can be prepared as follows:

(a) In a manner analogous to that described in Example 1(b), from (1S)-cis-3-ethyl-1,2,3,4,5,12-hexahydro-5,12-dioxo-1,3-naphthacenediyl benzeneboronate there was obtained (1S)-cis-5,12-diacetoxy-3-ethyl-1,2,3,4-tetrahydro-1,3-naphthacenediyl benzeneboronate which was used in the next step without purification.

(b) Oxidation of (1S)-cis-5,12-diacetoxy-3-ethyl-1,2,3,4-tetrahydro-1,3-naphthacenediyl benzeneboronate in a manner analogous to that described in Example 1(c) gave (1S)-cis-5,12-diacetoxy-3-ethyl-1,2,3,4,6,11-hexahydro-6,11-dioxo-1,3-naphthacenediyl benzeneboronate which was used in the next step without purification.

(c) Treatment of (1S)-cis-5,12-diacetoxy-3-ethyl-1,2,3,4,6,11-hexahydro-6,11-dioxo-1,3-naphthacenediyl benzeneboronate with boron trichloride in a manner analogous to that described in Example 1(d) gave (1S)-cis-3-ethyl-1,2,3,4,6,11-hexahydro-5,12-dihydroxy-6,11-dioxo-1,3-naphthacenediyl benzeneboronate which was used in the next step without purification.

(d) In a manner analogous to that described in Example 1(e), from (1S)-cis-3-ethyl-1,2,3,4,6,11-hexahydro-6,11-dioxo-1,3-naphthacenediyl benzeneboronate there was obtained (1S)-cis-3-ethyl-1,2,3,4,6,11-hexahydro-1,3,5,12-tetrahydroxy-6,11-dioxonaphthacene of melting point 179°–183° C.; $[α]_D^{20} = +136.2°$ (c=0.1% in dioxan).

The (1S)-cis-3-ethyl-1,2,3,4,5,12-hexahydro-5,12-dioxo-1,3-naphthacenediyl benzeneboronate used as the starting material in paragraph (a) of this Example can be prepared as follows:

(i) 12.95 g of a 50% dispersion of sodium hydride in mineral oil were added to 152 ml of dry dimethyl sulphoxide stirred under nitrogen. The mixture was stirred at 70° C. until the evolution of hydrogen had ceased. After cooling to 0° C., 152 ml of dry tetrahydrofuran were added. 20.30 g of methyl (S)-1',2',3',4'-tetrahydro-2'-hydroxy-5',8'-dimethoxyspiro[1,3-dithiolane-2,4'-naphthalene]-2'-carboxylate, prepared as described in Example 1(vi), in 152 ml of dry tetrahydrofuran were added dropwise over a period of 10 minutes. After stirring at 0° C. for 15 minutes, the mixture was poured into 1000 ml of water and acidified to pH 3 with hydrochloric acid. The solution was extracted with four 400 ml portions of dichloromethane. The combined dichloromethane extracts were washed with 650 ml of water, dried over magnesium sulphate and evaporated to give the crude β-ketosulphoxide in the form of an orange oil which was used without further purification.

The crude β-ketosulphoxide obtained as described in the preceeding paragraph was dissolved in a mixture of 985 ml of tetrahydrofuran and 98.5 ml of water. The solution was stirred under nitrogen and cooled to 12° C. Aluminium amalgam (prepared from 15.2 g of aluminium foil) was added and the mixture was stirred for 2 hours while maintaining the temperature at 12°–15° C. The mixture was then filtered and the tetrahydrofuran was removed by evaporation. The residue was dissolved in 530 ml of dichloromethane and the solution was washed with two 1000 ml portions of water, dried over magnesium sulphate and evaporated to give a cream coloured solid. Recrystallisation from dichloromethane/diethyl ether gave 11.55 g (60%) of (S)-3'-acetyl-1',2',3',4'-tetrahydro-3'-hydroxy-5',8'-dimethoxyspiro[1,3-dithiolane-2,1'-naphthalene] in the form of colourless crystals of melting point 175°–178° C.; $[α]_D^{20} = -25.3°$ (c=0.5% in chloroform).

(ii) 16.48 g of (S)-3'-acetyl-1',2',3',4'-tetrahydro-3'-hydroxy-5',8'-dimethoxyspiro[1,3-dithiolane-2,1'-naphthalene] were suspended in 1450 ml of dry tetrahydrofuran and 3.59 g of sodium borohydride were added to the mixture. The mixture was then stirred at room temperature under nitrogen for 4 hours. The solvent was removed by evaporation and the white residue was cooled to 0° C. 1500 ml of 5% ammonium chloride solution were added and the mixture was stirred at room temperature until the evolution of gas had ceased. The solution was extracted with three 500 ml portions of ethyl acetate and the combined ethyl acetate extracts were washed with 1000 ml of water, dried over magnesium sulphate and evaporated to give 17.65 g of (3'S)-1',2',3',4'-tetrahydro-3'-hydroxy-3'-(1-hydroxyethyl)-5',8'-dimethoxyspiro[1,3-dithiolane-2,1'-naphthalene] in the form of a colourless gum which was used without further purification.

(iii) 17.65 g of (3'S)-1',2',3',4'-tetrahydro-3'-hydroxy-3'-(1-hydroxyethyl)-5',8'-dimethoxyspiro[1,3-dithiolane-2,1'-naphthalene] were dissolved in 380 ml of dry pyridine and the solution was stirred under nitrogen and cooled to 0° C. A solution of 5.55 g of methanesulphonyl chloride in 50 ml of dry pyridine was added and the mixture was left to stand at 4° C. for 18.5 hours. The pyridine was removed by evaporation, 500 ml of water and 250 ml of ethyl acetate were added to the residue and the mixture was stirred for 10 minutes. The layers were separated and the aqueous layer was extracted with a further three portions of 250 ml of ethyl acetate. The combined ethyl acetate extracts were washed with two 500 ml portions of water, two 500 ml portions of 2M hydrochloric acid and 500 ml of saturated sodium hydrogen carbonate solution, dried over magnesium sulphate and evaporated to give 20.74 g of 3',4'-dihydro-3'-hydroxy-5',8'-dimethoxy-α-methylspiro[1,3-dithiolane-2,1'(2'H)-naphthalen]-3'-ylmethyl methanesulfonate in the form of a colourless gum which was used without further purification.

(iv) A mixture of 3.68 g of lithium aluminium hydride and 200 ml of dry tetrahydrofuran was stirred under nitrogen. A solution of 20.74 g of 3',4'-dihydro-3'-hydroxy-5',8'-dimethoxy-α-methylspiro[1,3-dithiolane-2,1'(2'H)-naphthalen]-3'-ylmethyl methanesulfonate in 300 ml of dry tetrahydrofuran was added. The mixture was stirred and heated under reflux for 50 minutes and subsequently cooled to 0° C. 110 ml of 10% ammonium chloride solution were added and the mixture was evaporated in order to remove the tetrahydrofuran. 1000 ml of 2M hydrochloric acid were added to the residue and the mixture was extracted with three 500 ml portions of ethyl acetate. The combined ethyl acetate extracts were washed with 500 ml of saturated sodium hydrogen carbonate solution, dried over magnesium sulphate and evaporated to give 15.31 g of (S)-3'-ethyl-1',2',3',4'-tetrahydro-3'-hydroxy-5',8'-dimethoxyspiro[1,3-dithiolane-2,1'-naphthalene] in the form of a colourless gum which was used without further purification.

(v) In a manner analogous to that described in Example 1(ix), from 15.31 g of (S)-3'-ethyl-1',2',3',4'-tetrahydro-3'-hydroxy-5',8'-dimethoxyspiro[1,3-dithiolane-2,1'-naphthalene] there were obtained 7.38 g (63%) of (S)-3-ethyl-1,2,3,4-tetrahydro-3-hydroxy-5,8-dimethoxy-1-oxo-naphthalene in the form of a white powder of melting point 132°–134° C.

(vi) A solution of 7.38 g of (S)-3-ethyl-1,2,3,4-tetrahydro-3-hydroxy-5,7-dimethoxy-1-oxo-naphthalene in 490 ml of dry tetrahydrofuran was stirred and 1.73 g of lithium borohydride were added. The mixture was stirred at room temperature for 70 minutes and was then evaporated in order to remove the tetrahydrofuran. 250 ml of 10% ammonium chloride solution were added to the residue and the mixture was extracted with three 250 ml portions of ethyl acetate. The combined ethyl acetate extracts were washed with 250 ml of water and dried over magnesium sulphate. After filtration, the filtrate was treated with 3.86 g of benzeneboronic acid and 0.6 ml of acetic acid. The solution was stirred and heated under reflux for 45 minutes and then the solvent was removed by evaporation. The residue was dissolved in 650 ml of toluene and the solution was treated with 1.93 g of benzeneboronic acid and 0.197 g of p-toluenesulphonic acid. The mixture was stirred at room temperature for 16.5 hours. The solution was washed with two 250 ml portions of 10% potassium hydrogen carbonate solution, dried over magnesium sulphate and evaporated to give 9.18 g (92%) of (1S)-cis-3-ethyl-1,2,3,4-tetrahydro-5,8-dimethoxy-1,3-naphthalenediyl benzeneboronate in the form of white crystals of melting point 132°–133° C.; $[\alpha]_D^{20} = +56.0°$ (c=0.5% in chloroform).

(vii) A solution of 9.15 g of (1S)-cis-3-ethyl-1,2,3,4-tetrahydro-5,8-dimethoxy-1,3-naphthalenediyl benzeneboronate in 400 ml of acetonitrile was stirred and a solution of 29.83 g of ammonium ceric nitrate in 400 ml of water was added over a period of 5 minutes. The mixture was stirred at room temperature for 5 minutes and then poured into 2200 ml of water. The resulting mixture was extracted with five 270 ml portions of dichloromethane and the combined dichloromethane extracts were washed with 550 ml of water, dried over magnesium sulphate and evaporated to give 8.23 g of (1S)-cis-3-ethyl-1,2,3,4-tetrahydro-5,8-dioxo-naphthalenediyl benzeneboronate in the form of a yellow gum which was used without further purification.

(viii) 8.23 g of (1S)-cis-3-ethyl-,1,2,3,4-tetrahydro-5,8-dioxy-naphthalenediyl benzeneboronate and 7.48 g of trans-1,2-diacetoxy-1,2-dihydrobenzocyclobutene were dissolved in 500 ml of xylene and the mixture was stirred at 140° C. for 195 minutes. The xylene was removed by evaporation and the residue was stirred with 200 ml of ether and subsequently filtered to give 7.96 g (72%) of (1S)-cis-3-ethyl-1,2,3,4,5,12-hexahydro-5,12-dioxo-1,3-naphthacenediyl benzeneboronate in the form of a bright yellow solid of melting point 225°–226° C.; $[\alpha]_D^{20} = +143.3°$ (c=0.1% in chloroform).

What is claimed is:
1. A compound of the formula

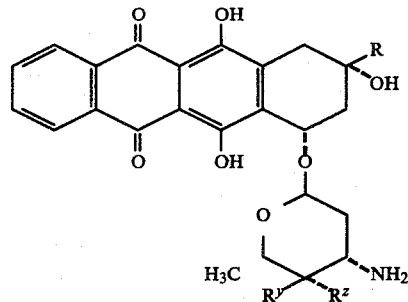

wherein R is a lower alkyl but not ethyl or carboxy or a group of the formula

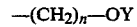    a in which n stands for 1 or 2 and Y is hydrogen or lower alkyl and $R^Y$ and $R^z$ each are hydrogen or one of $R^Y$ and $R^z$ is hydrogen and the other is hydroxy, and pharmaceutically acceptable acid addition salts thereof.

2. The compound of claim 1, wherein R is lower alkyl but not ethyl or a group of formula (a) in which Y is hydrogen.

3. The compound of claims 1 or 2, wherein one of $R^Y$ and $R^z$ is hydrogen and the other is hydroxy.

4. The compound: (1S)-cis-1-[(3-Amino-2,3,6-trideoxy-α-L-lyxohexopyranosyl)oxy]-1,2,3,4,6,11-hexahydro-3,5,12-trihydroxy-3-hydroxymethyl-6,11-dioxonaphthacene.

5. The compound: (1S)-cis-1-[(3-Amino-2,3,6-trideoxy-α-L-lyxohexopyranosyl)oxy]-1,2,3,4,6,11-hexahydro-3,5,12-trihydroxy-3-methyl-6,11-dioxonaphthacene.

6. The compound: (1S)-cis-1-[(3-Amino-2,3,6-trideoxy-α-L-arabinohexopyranosyl)oxy]-1,2,3,4,6,11- hexahydro-3,5,12-trihydroxy-3-methyl-6,11-dioxonaphthacene.

7. The compound: (1S)-cis-1-[(3-amino-2,3,6-trideoxy-α-L-arbinohexopyranosyl)oxy]-1,2,3,4,6,11-hexahydro-3,5,12-trihydroxy-3-hydroxymethyl-6,11-dioxonaphthacene.

8. The compound: (1S)-cis-1-[(3-amino-2,3,6-trideoxy-α-L-lyxohexopyranosyl)oxy]-3-ethyl-1,2,3,4,6,11-hexahydro-3,5,12-trihydroxy-6,11-dioxonaphthacene.

9. A compound of the formula

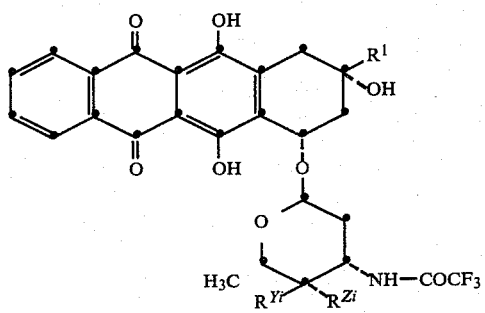

wherein $R^1$ is lower alkyl but not ethyl or an alkoxycarbonyl, phenoxycarbonyl or benzyloxycarbonyl group or a group of the formula

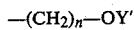

where n is 1 or 2 and Y' is lower alkyl, alkanecarboxyl, benzyl or phenylcarboxyl and $R^{Yi}$ and $R^{Zi}$ each are hydrogen or one of $R^{Yi}$ and $R^{Zi}$ is hydrogen and the other is p-nitrobenzoyloxy.

* * * * *

UNITED STATES PATENT AND TRADEMARK OFFICE
CERTIFICATE OF CORRECTION

PATENT NO. : 4,591,636

DATED : May 27, 1986

INVENTOR(S) : Michael J. Broadhurst et al.

It is certified that error appears in the above-identified patent and that said Letters Patent is hereby corrected as shown below:

In claim 1, the first chemical formula (formula I) should be as follows:

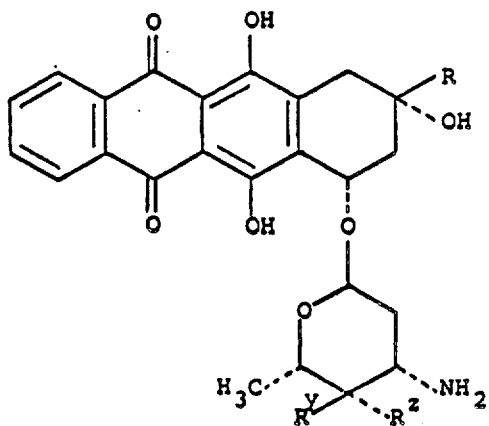

UNITED STATES PATENT AND TRADEMARK OFFICE
CERTIFICATE OF CORRECTION

PATENT NO. : 4,591,636

DATED : May 27, 1986

INVENTOR(S) : Michael J. Broadhurst et al.

It is certified that error appears in the above-identified patent and that said Letters Patent is hereby corrected as shown below:

In claim 9, the chemical formula should be as follows:

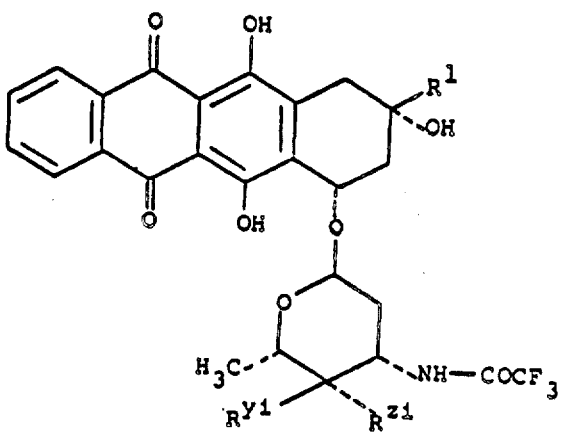

Signed and Sealed this

Twelfth Day of July, 1988

Attest:

DONALD J. QUIGG

Attesting Officer

Commissioner of Patents and Trademarks